United States Patent [19]

Schwartz et al.

[11] 4,177,945
[45] Dec. 11, 1979

[54] HUMIDIFIER UNIT

[75] Inventors: Charles M. Schwartz, Columbus, Ohio; Eugene J. Meierhoefer, Hackettstown, N.J.

[73] Assignee: Warner-Lambert Company, Morris Plains, N.J.

[21] Appl. No.: 883,609

[22] Filed: Mar. 6, 1978

[51] Int. Cl.² .................. A61M 11/02; B05B 7/30
[52] U.S. Cl. .................. 239/338; 128/200.18; 261/78 A; 261/DIG. 65; 128/200.21
[58] Field of Search .......... 239/272, 309, 338, 346, 239/347, 370; 128/191 R, 194; 261/78 A, DIG. 65

[56] References Cited

U.S. PATENT DOCUMENTS

| | | | |
|---|---|---|---|
| 3,075,523 | 1/1963 | Eichelman | 239/338 X |
| 3,652,015 | 3/1972 | Beall | 239/338 |
| 3,836,079 | 9/1974 | Huston | 239/338 X |
| 3,903,216 | 9/1975 | Allan et al. | 261/78 A |
| 3,913,843 | 10/1975 | Cambio | 239/338 |
| 3,915,386 | 10/1975 | Vora | 239/338 |
| 4,036,919 | 7/1977 | Komendowski et al. | 261/DIG. 65X |

Primary Examiner—Johnny D. Cherry
Attorney, Agent, or Firm—Albert H. Graddis

[57] ABSTRACT

Humidifier and nebulizer adapter heads and humidifier assembly for inhalation therapy wherein high moisture content can be provided in a gas stream at high flow rates. The humidifier assembly consists of a disposable bottle and the disposable humidifier adapter head. The adapter head employs a conventional nebulizer to create a dense aerosol of sterile water and/or medicament entrained in an oxygen/air stream. The stream passes through a labyrinth of wide baffles which forces the stream to take a tortuous path resulting in turbulent flow and a high removal of droplets from the gas stream, but without generating a significant back pressure. The large surface area deflectors of the labyrinth also allow higher humidity of the gas stream due to evaporation. Water removed from the gas stream drains directly to the bottle.

13 Claims, 5 Drawing Figures

HUMIDIFIER UNIT

BACKGROUND OF THE INVENTION

In one form of respiratory therapy, the patient receives oxygen or a mixture of oxygen and air. In order to avoid dehydration, discomfort, and damage to the lungs, it is necessary that the gas be humidified to a high moisture content. Certain treatment calls for a dense aerosol or mist of water droplets to be carried by the oxygen or mixture to the patient (generally by means of a tent). This is accomplished in present practice, either by use of a venturi nebulizer operated by the oxygen stream, or when an extremely dense fog is indicated, by means of an ultrasonic nebulizer. In many cases, however, the use of a mist is contraindicated, and the present invention is concerned with a device that will provide, as prescribed, either a high level of humidification of oxygen delivered with a minimum of entrained droplets, or a dense aerosol in oxygen or air/oxygen mixture.

In a common form of humidifier in the prior art, one simply passes bubbles of the gas, generated in some form of sparger, up through a head of water contained in a reservoir. This method is unsatisfactory in that the humidity obtainable is low and is not constant, diminishing as the level of water in the container falls as it vaporizes during the course of treatment. Also, bubbles are objectionably noisy.

Another method available is described in U.S. Pat. No. 3,913,843 (Cambio). This device employs the same venturi nebulizer conventionally used to create an aerosol or mist, then entrains the droplets in a foraminous member, so that only the humidified gas passes into the exit stream to the patient. The aerosol droplets are entrained and the liquid is returned to the reservoir by an extra tube which is somewhat of a nuisance and may also be the source of pressure leaks. The foraminous member is described as a reticulated polyurethane foam or any foraminous material, such as a microporous filter in which the atomized droplets may be entrained or interstitially held. This device is less than satisfactory in that the filter causes an appreciable pressure drop, the maximum humidity obtainable at high flow-rate is insufficient, and the maximum flow rate may be too low.

In the application of respiratory therapy, it is highly desirable that sterile water be used to humidify the oxygen stream, and it is advantageous that the container be a factory-filled and sealed, disposable package. Designs which may cause contamination of the sterile water (or medicament) when assembled at bedside are not satisfactory.

Prior U.S. patents which show humidifiers include U.S. Pat. Nos. 3,836,079; 2,709,577; and 3,652,015. U.S. Pat. No. 3,075,523 shows a nebulizer which includes a series of mesh screens designed to demist the larger aerosol droplets.

SUMMARY OF THE INVENTION

It is an object of the invention to provide both a nebulizer unit and a humidifier unit which are disposable and which comprise a sealed, sterile-liquid bottle and individual adapter heads designed for the desired output.

It is further an objective of the invention to provide a novel dual breaching system providing a sterile connection between bottle and adapter, direct recycle of excess sterile liquid from the adapter to the bottle and efficient seal between breaching members and the bottle.

It is a further objective that the adapter head for nebulization be interchangeable on the bottle with the adapter head for humidification.

It is also an objective of the invention to provide a humidifier unit which efficiently humidifies the gas stream and removes droplets therefrom at high gas flow rates but without high back pressures.

In accordance with the objectives the invention comprises a unit for producing an delivering an entrained liquid aerosol or molecular water (water vapor) in a pressurized gas stream. The aerosol is produced by a nebulizer unit comprising a novel bottle and a nebulizer adapter head. The humidified gas is produced by modifying the nebulizer adapter head into a humidifier adapter head which removes liquid droplets and evaporates additional liquid droplets into the gas stream.

The bottle comprises a reservoir section for the liquid and a duct attached at the bottom of the reservoir and extending up the side to the top. The duct carries liquid to the adapter heads during operation. The bottle also has an inlet for liquid being returned from the adapters to the bottle. Together, the liquid return inlet to the reservoir and the upper end of the duct form a single neck region which is threaded and engages a union nut (sealing ring) of the adapters. The inlet and duct are both sealed on their upper surfaces but are breachable by two separate cannulae on the adapters. An annular ridge on the adapter around one cannula seals the cannula to the duct in a vacuum-tight manner.

The bottle may also have an inlet for an immersion type heater or it may include a provision for a slide-on or wrap-around external type heater.

The nebulizer adapter head comprises a housing having an inlet for pressurized gas, an exit for the treated gas, and the two breaching cannulae below the inlet and exit openings and on the bottom wall of the housing. The cannulae are arranged to breach the duct and the liquid return inlet of the bottle. A seal ring or union nut encircles the bottom of the adapter for joining the adapter to the threaded neck member of the bottle. An annular ridge also surrounds the duct cannula for forming a vacuum-tight seal between the cannula and the duct.

The adapter further comprises a venturi means within the housing including a venturi channel for pressurized gas and a perpendicular liquid passage downstream of the venturi channel for supplying liquid to the passing gas stream by the Bernouli effect. Means are included for connecting the venturi channel to the pressurized gas stream and for forming a vacuum-tight connection between the liquid passage and the duct-breaching cannula.

The humidifier adapter head has the elements of the nebulizer head above and further includes a labyrinth of wide deflectors disposed transversely to the flow of aerosol. The labyrinth provides a tortuous path for the aerosol and a large surface area for impact and fractionation of droplets and the evaporation of molecular water for increasing humidity. Liquid coalesces on the deflectors and drops to the bottom of the adapter and returns to the bottle through the liquid return inlet.

The humidifier head may also include a safety valve which opens in case of a build-up in pressure. Both adapter heads may contain a target member downstream of the venturi means for impacting with aerosol.

The nebulizer may include a port means for inspiring air into the pressurized gas stream upstream of the venturi.

DETAILED DESCRIPTION OF THE INVENTION

Figure 1:
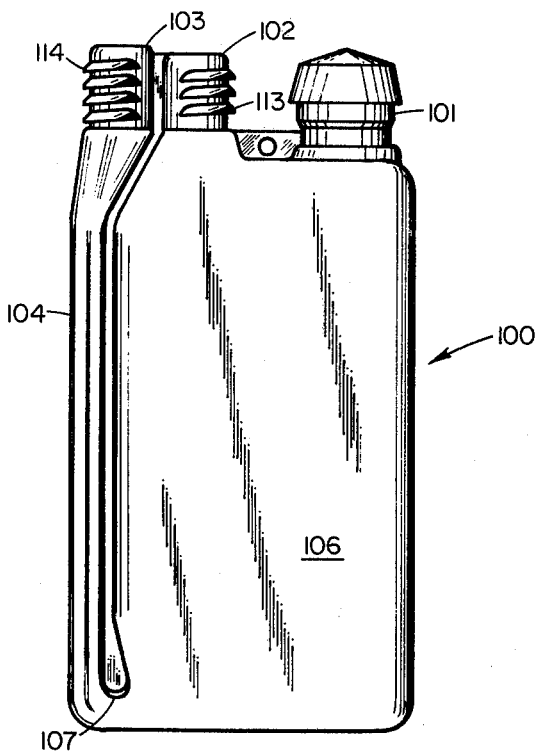
FIG. 1 is an elevation view of the novel bottle of the invention.

With a change in adapter heads, the present invention can deliver an aerosol or humidified gas to a patient. Humidified air is produced from an aerosol with the droplets of greater than a certain size removed. Smaller droplets then evaporate yielding molecular vapor in the air. In respiratory therapy the gas would normally be oxygen or air and the liquid would be sterile water.

Referring now to the drawings, the invention is a nebulizer or humidifier unit comprising a novel sealed bottle plus a compact disposable adapter head that upon assembly will sequentially breach the sealed bottle and couple thereto, effecting a liquid and vacuum tight seal. The breaching mechanism is unique, in that two passages are simultaneously generated during assembly, one to a duct leading to the bottom of the bottle, the other to the air space above the liquid in the bottle. The duct (or lift tube) to the reservoir bottom is the liquid passage to the nebulizer, water being lifted by the reduced pressure developed in the venturi of the nebulizer. The other passage returns "rain-out" or excess liquid collected in the adapter head. An exit orifice is provided for connection to tubing leading to the patient's mouthpiece, mask or tent.

In FIG. 1, 2 and 5, the special sealed, disposable bottle 100 is shown. It consists generally of two elements, a liquid reservoir 106 and a conduit, lift tube or duct 104 extending along one side of the reservoir. The reservoir 106 and the duct 104 are in liquid communication at the bottom of the bottle and in this case are integrally formed with a liquid passage 107 therebetween. The passage is preferably close to the bottom of the bottle so that most of the liquid is removed during use. The duct, as shown best in FIG. 5, is shaped with a necked-in region 116 at the bottom to enable a slide-on heater to be applied around the duct from the bottom and a tapered region 117 which may act as a stop for the slide-on heater.

On the top of the reservoir on the side nearest the duct 104, is a liquid return member 102 which has an upwardly extending hemi-cylindrical shape and male threads 113 around the arcuate portion. The liquid return member has a breachable seal 109 covering the upper portion thereof.

The duct 104 also has an extension 103 extending to a level slightly higher than that of the liquid return member 102. The duct extension 103 is likewise hemi-cylindrical in shape and has male threads 114 therearound on its arcuate portion. Liquid return member 102 and duct extension 103 cooperate to form a longitudinally-split, cylindrical neck portion 115 having a discontinuous male thread therearound for attachment to the adapter head shown in FIG. 3. Duct extension 103 is closed with a breachable seal 108 covering the upper portion thereof.

The breachable seals 108 and 109 are adapted to be breached at positions 111 and 112, respectively, by breaching cannulae in the adapter head. An annular ridge of the adapter head forms a vacuum-tight seal by pressure contact with breachable seal 108 at a position shown as dotted line 110.

An immersion type heater may be used with the bottle by inserting through optional heater port 101. Alternatively, a wrap-around type heater can be used around the entire bottle 100 or a slide-on heater may be applied to the duct 104 cooperating with the special shape at the bottom of the duct at 116.

The bottle is preferably integrally molded from a low-cost disposable material, such as a polyethylene, polypropylene, polycarbonate or other thermosplastic material. The bottle can be efficiently molded, filled with sterile liquid and sealed in one operation.

Referring now to FIg. 3, a disposable humidifier adapter head 1 is shown. It is preferably assembled from several preformed pieces of low-cost disposable materials such as named above for the bottle. An integral housing 2 in the general shape of a cylinder has a collar member 22 extending axially upward and a humidified gas exit 5 extending radially outward for attachment of a hose to transport the humidified gas to the patient. The housing further includes a support post 26 extending upwardly and cannulae 7 and 8 extending downwardly from a bottom member 9 which is sealed to the housing 2. The cannulae are downwardly tapered and located such that they may breach the breachable seals 108 and 109 of the bottle at locations indicated by dotted circles 111 and 112 in FIG. 2. An annular ridge member 10 surrounds cannula 7 on the outside surface of the bottom member 9 for contacting the breachable seal 108 of the duct extension 103 and sealing the cannula 7 to the duct extension 103 in a vacuum-tight manner.

A safety valve 6 may also be formed integrally with the housing. In the safety valve shown (duck bill valve), flexible opposed members 27 are normally closed against each other preventing escape of low pressure gas from the adapter head through relief opening 3. If, however, the pressure increases due, for example, to a crimping of the hose leading to the patient, the higher pressure gas will bend the flexible opposed members 27 away from each other and allow the pressure to be relieved. Other valves such as poppet, Bunsen or reed could be used.

The housing is closed by circular bottom member 9 which may be assembled and glued or welded as by ultrasonics or snap fitted into the housing using for example, an annular bead in the bottom member and a complementary groove in the housing.

A downwardly extending cylindrical labyrinth support 17 is located within the housing and may be snap fitted into position. Labyrinth 11 is supported in housing 2 by support 17 and also by post 26. Gas fitting 19 is sealed to the collar 22 of the housing.

The gas fitting 19 includes a rounded upper surface 21 which coacts with a pressurized gas source, and a large axial bore 18 for directing pressurized gas to a small venturi channel 14 in a sleeve member 28 where the gas is forced out at a high velocity. The gas fitting may be conveniently sealed to a pressurized gas source by means of an upper union nut 20.

The sleeve member 28 has a cylindrical top portion which fits within the collar 22 and a downwardly extending portion which is supported on a ledge of the labyrinth support 17. A vertical guide hole 25 and a small horizontal liquid passage 13 extending from the vertical guide hole 25 and terminating in a liquid aperture 15 at a point immediately downstream of the venturi channel 14 are formed in the lower portion of the sleeve member 28. A cylindrical deflector 16 may be optionally formed in the lower portion of the sleeve member further downstream of the venturi channel 14 and the horizontal liquid aperture 15.

A liquid conduit 12 extends from the breaching cannula 7 to the guide hole 25 and forms a vacuum-tight seal on each end by means of a tight friction fit into the tapered guide hole and cannula. A sealing glue may be used if necessary.

The final member inside the housing is the labyrinth 11 of transverse deflectors 29 for demisting the aerosol produced by the nebulizer. The labyrinth is supported and positioned by the labyrinth support 17 and the support post 26. It has a vertical hole 23 therethrough for accepting the liquid conduit 12. The labyrinth has a cylindrical shell and multiple deflectors 29, which for example may be transverse to the shell similar to chords of a circle.

Various other forms of deflector geometry may be employed. Each design is characterized by an "opaque" geometry, that is, with no direct unobstructed flow path. Instead, each design ensures that flow of the aerosol occurs over a tortuous path, providing large areas of wet surface, upon which the droplets are caused to impact, and from which molecular water evaporates as vapor. The labyrinth path creates turbulent flow of the oxygen aerosol, to assure adequate opportunity for contact with many surfaces, and therefore, to provide essentially complete rainout, or demisting. The pressure drop across such a baffle is quite low. The labyrinths have been tested at low gas flow rates and found to produce up to 75 percent RH of oxygen at room temperature, with complete removal of droplets. Moreover, the labyrinth designs performed equally well at high flow rates (up to 14 l/min.) with negligible back pressure.

Figure 3:
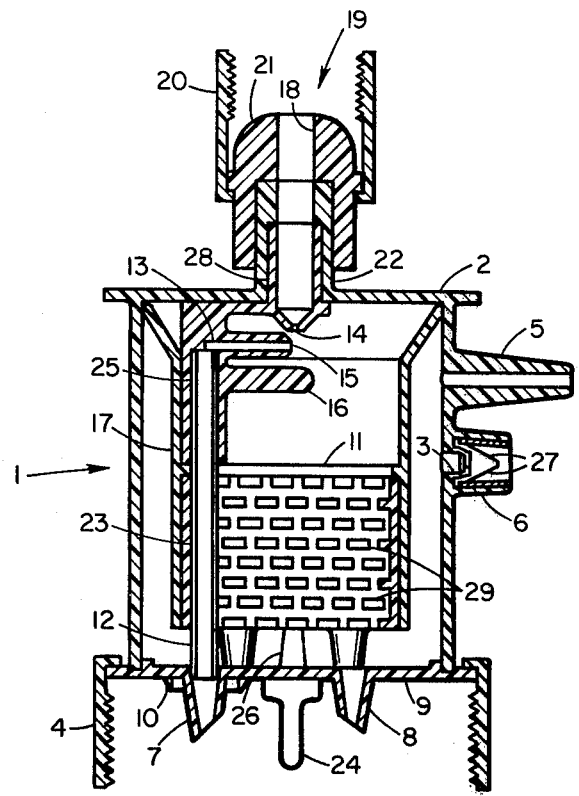
FIG. 3 is a vertical view, partly in section, of the humidifier adapter head.

The labyrinth deflectors can take many forms. FIG. 3 shows a multi-comb assembly, with uniform rows of deflectors but with staggered columns. This provides the necessary opacity, turbulent flow and large surface area for droplet impact, rainout and evaporation. The comb posts of FIG. 3 need not be rectangular in section, as shown, but may be cylindrical, elliptical, triangular, or lozenge in shape, with similar effectiveness, provided that the geometry generates a suitable flow pattern, as specified above.

For good removal of droplets and for negligible back pressure, we have found that for any horizontal cross-section through the rows of deflectors, a minimum or 25–50% of the total area should be open (i.e., void). For example, if the deflectors are arranged as in FIG. 3 but are triangular in shape, the minimum opening would occur in the plane of the bases of the triangles and not between the apexes and should be between 25 and 50% of the total area of the cross-section. The spacing between rows should not be so small that an appreciable increase in back pressure occurs over the pressure through one row. Preferably, the spacing between rows is at least equal to the spacing between adjacent deflectors in a row.

The labyrinth may be made of any of the above mentioned low-cost plastics, or additionally of methacrylate, for the reason that it is more easily wet by water which may increase the ability of demisting the aerosol. Alternatively, the labyrinth may be coated with a material easily wet by water or other liquid used.

Figure 2:
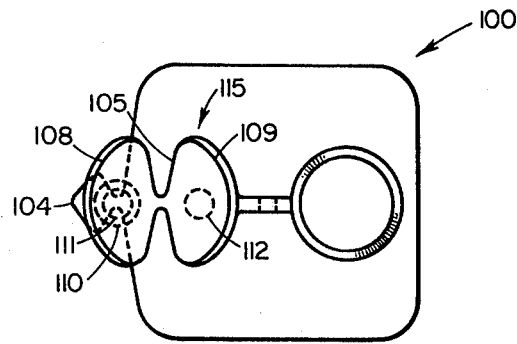
FIG. 2 is a plan view of the bottle.

The humidifier adapter head just described may be fastened to the earlier described bottle by means of a union nut 4 which engages the periphery of the bottom member 9 and is internally threaded to engage the threaded neck portion 115 of bottle 100 and to cause the breaching cannulae to breach the seals 108 and 109 and form a vacuum-tight seal with annular ridge 10. A positioning finger 24 extends downwardly from the bottom member for cooperating with region 105 (in FIG. 2) formed by liquid return member 102 and duct extension 103 to prealign the union nut with the threaded neck portion.

The nebulizer adapter head comprises the same elements and is formed in the same fashion (for interchangeability) as the humidifier adapter head shown in FIG. 3 with the following exceptions:

(1) The safety valve 6 is generally not required since the aerosol is used in a tent rather than in a patient mask.

(2) The labyrinth 11 is not necessary since removal of droplets is not required.

Figure 4:
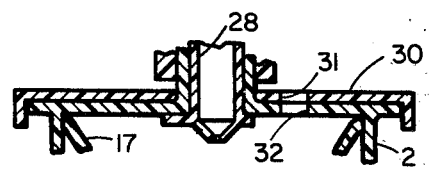
FIG. 4 is a breakaway view of FIG. 3 showing a modification of the nebulizer adapter head wherein air may be inspired into the aerosol at controlled ratios.
Figure 5:
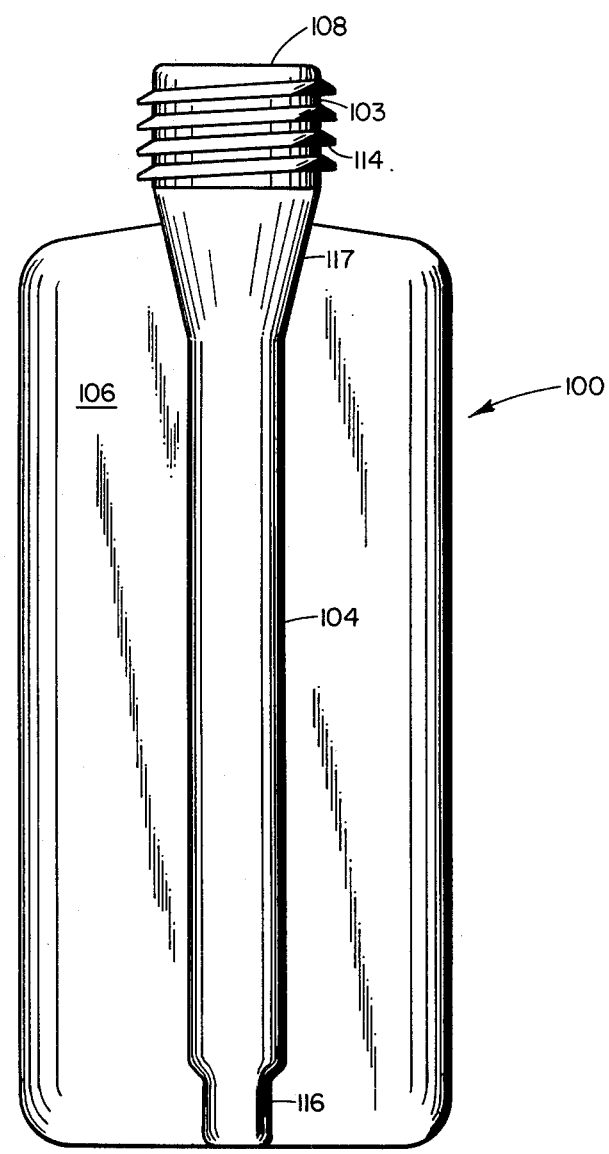
FIG. 5 is a side elevation view of the bottle of FIG. 1 showing the special shape of the duct for accommodating a slide-on heater over the duct.

(3) An inspiration valve such as shown in FIG. 4 may be added to mix air into the pressurized gas.

As shown in breakaway section in FIG. 4, the top of the housing 2 of the nebulizer adapter contains an additional orifice or slot 32 and is covered by a rotatable disc 30 having an orifice or slot 31 in the same radial position as the orifice 32. By rotating the disc 30, the orifices may be made coaxial or non-overlapping or any relation therebetween. Thus the percentage of air inspired by reason of the low-pressure region within the housing and created by the venturi action may be regulated by rotating the disc 30 to precalibrated positions. Labyrinth support 17 is upwardly, outwardly tapered to provide a venturi effect for the inspiration of air through orifices 31 and 32.

In practice, the humidifier operates in the following fashion. The sealed, disposable bottle 100 containing sterile liquid is breached by the two cannulae 7 and 8 of the sterilized adapter head 1. The positioning finger 24 is located in the region 105 of the bottle and the union nut 4 of the adapter head is tightened on the threaded neck portion 115 of the bottle. This brings the annular ridge 10 into pressured contact with breachable duct seal 108 forming a vacuum-tight seal between the duct 104 and the breaching cannula 7. The bottom member and cannula 8 are also pressured against the breachable seal 109 forming a weak pressure seal. This seal need not be a vacuum-tight seal since the gas pressure at this point is very low, routinely less than 1 psig.

When firmly attached to the bottle, the adapter head is connected with a source of pressurized gas so that the gas enters through axial bore 18 in gas fitting 19 and is forced through venturi channel 14. By the Bernoulli effect, the rapidly moving gas passing from the venturi channel 14 causes a lowering of pressure in a region downstream thereof and in the area of the liquid aperture 15. This lower pressure region then causes liquid to be forced up the duct 104 from the reservoir 106, through the liquid conduit 12, and through horizontal liquid passage 13 and out the liquid aperture 15. This liquid is entrained in the gas stream and is impacted against the cylindrical deflector 16 to further break up the liquid into fine droplets.

This aerosol then passes through the labyrinth 11 herein the fine droplets coalesce on the large surface area deflectors 29 and drain through the labyrinth to the bottom of the housing, returning to the bottle directly through the cannula 8. Some of the liquid on the surface of the deflectors evaporates to further raise the humidity of the treated gas. The treated gas then passes out the exit 5 to the intended use area.

The nebulizer adapter head works in the same fashion as the humidifier, but the aerosol is not demisted. Some larger droplets still coalesce, however, and are returned to the bottle. Additionally, the inspiration valve may be controlled to affect the mixture of pressurized gas and air in the aerosol.

We claim:

1. A unit for producing an entrained liquid aerosol in a pressurized gas stream comprising a vacuum-tight bottle for supplying the liquid and an adapter head for coupling the liquid pressurized gas stream,
  (A) wherein the bottle comprises
    (i) reservoir means for the liquid including a breachable seal,
    (ii) connecting means including a breachable seal for communicating with the liquid in the reservoir means and supplying the liquid through a liquid passage to the adapter head, and
  (B) wherein the adapter head comprises
    (iii) housing means having an inlet opening for pressurized gas, an exit opening for aerosol laden pressurized gas and first and second breaching cannulae below the inlet and exit openings and on the lower extreme of the housing means,
      the first cannula breaching the breachable seal of the connecting means for communicating with the liquid so as to be in liquid communication with the reservoir means, the second cannula breaching the breachable seal on the reservoir means so as to be in communication with the reservoir means for returning excess liquid from the housing means to the reservoir means,
    (iv) means forming a vacuum-tight seal between the first cannula and the connecting means for communicating with the liquid in the reservoir,
    (v) venturi means fixed within the housing means including a venturi channel and a perpendicular liquid passage operatively associated with the venturi channel and downstream thereof so that the pressure drop of gas passing through the venturi channel causes liquid droplets from the liquid passage to be inspired therein,
    (vi) means for connecting the venturi channel with the pressurized gas stream, and
    (vii) means forming a vacuum-tight connection between the liquid passage and the first cannula whereby the liquid passage is in liquid communication with the reservoir means.

2. A unit for producing an entrained liquid aerosol in a pressurized gas stream comprising a vacuum-tight bottle for supplying a quantity of the liquid and an adapter head adapted to couple the pressurized gas stream to the liquid,
  (A) wherein the bottle comprises
    (i) reservoir means for the liquid including an upwardly extending, liquid return member having a breachable seal on an upper surface thereof, and
    (ii) duct means communicating with the liquid for the passage of the liquid from the reservoir means to the adapter head including a duct extension on the upper extreme of the duct means and a breachable seal on an upper surface thereof,
      the duct extension and the liquid return member of the reservoir means cooperatively forming a neck portion, and (B) wherein the adapter head comprises
    (iii) housing means having an inlet opening for pressurized gas, an exit opening for treated pressurized gas and first and second breaching cannulae below the inlet and exit openings and on the lower extreme of the housing means,
      the first cannula breaching the duct extension seal so as to be in liquid communication with the reservoir means, the second cannula breaching the seal on the reservoir liquid return member so as to be in communication with the reservoir means for returning excess liquid from the housing means to the reservoir means,
    (iv) means forming a vacuum-tight seal between the first cannula and the duct extension,
    (v) venturi means fixed within the housing means including a venturi channel and a perpendicular liquid passage operatively associated with the venturi channel and downstream thereof so that the pressure drop of gas passing through the venturi channel causes liquid droplets from the liquid passage to be inspired therein,
    (vi) means for connecting the venturi channel with the pressurized gas stream, and
    (vii) means forming a vacuum-tight connection between the liquid passage and the first cannula whereby the liquid passage is in liquid communication with the reservoir means.

3. The unit as in claim 2 wherein the liquid return member and the duct extension are each hemi-cylindrical in shape with threads therearound on the arcuate portions and wherein the duct extension and the liquid return member thereby cooperatively form a split-cylindrical neck portion having a discontinuous thread therearound.

4. The unit as in claim 3 wherein the means forming a vacuum-tight seal includes means for tightly biasing the lower extreme of the adapter head into contact with the upper surfaces of the liquid return member and duct extension of the bottle and for causing the breaching cannulae to breach the upper surfaces.

5. The unit as in claim 2 wherein air is mixed with the aerosol comprising means within the housing means for admitting controlled volumes of air in a region near the venturi means.

6. The unit as in claim 5 wherein the means for admitting controlled volumes of air comprises a top member of the housing means having an orifice therethrough communicating the inside of the housing means with the air atmosphere and a rotatable disc covering the top member and having an orifice adapted to overlap the orifice in the top member at one relative position of the top member and the rotatable disc and to not overlap the orifice of the top member at other relative positions thereof.

7. A unit as in claim 2 wherein liquid droplets are further removed from the aerosol and a humidified gas stream substantially devoid of liquid droplets is delivered to the exit opening wherein the adapter head further comprises (viii) a labyrinth of wide deflectors downstream of the venturi means arranged in an opague geometry for causing turbulent flow of the aerosol and coalescence of the liquid droplets on the deflectors.

8. A unit as in claim 7 comprising safety means for releasing the pressure within the adapter head when the pressure exceeds a predetermined safe level.

9. A unit as in claim 7 wherein the liquid is fractionated after leaving the liquid passage comprising a single deflector located immediately between the venturi channel and the labyrinth, downstream of the liquid passage.

10. A unit as in claim 7 wherein the means forming a vacuum-tight seal between the first cannula and the duct extension comprises an annular ridge surrounding the first cannula on the outside surface of the housing means for contacting the breachable seal on the upper surface of the duct extension.

11. A unit as in claim 7 wherein the labyrinth deflectors are arranged such that for any cross-sectional cut perpendicular to the flow direction of aerosol, 25–50% of the cross-sectional area of the labyrinth is open to the flow of aerosol.

12. A unit as in claim 11 wherein the labyrinth deflectors are arranged in parallel rows and staggered columns.

13. A unit as in claim 12 wherein the spacing between rows is at least equal to the spacing between adjacent deflectors in a row.

* * * * *